United States Patent [19]

Yong et al.

[11] Patent Number: 4,952,699
[45] Date of Patent: Aug. 28, 1990

[54] LIQUID-CRYSTALLINE, 2,5-DISUBSTITUTED, 1,3,4-THIADIAZOLES WITH EXTENDED SMECTIC C PHASES

[75] Inventors: Bak G Yong; Dietrich Demus; Horst Kresse; Annelore Mädicke, all of Halle; Gerhard Pelzl, Halle-Neustadt; Wolfgang Schäfer, Potsdam; Carsten Tschierske; Horst Zaschke, both of Halle, all of German Democratic Rep.

[73] Assignee: VEB Werk fuer Fernsehelektronik im VEB Kombinat Mikroelektronik, Berlin, German Democratic Rep.

[21] Appl. No.: 209,400

[22] Filed: Jun. 20, 1988

[30] Foreign Application Priority Data

Jul. 1, 1987 [DD] German Democratic Rep. ... 304402
Nov. 17, 1987 [DD] German Democratic Rep. ... 309119

[51] Int. Cl.$^5$ .................. C07D 285/12; C07D 285/14
[52] U.S. Cl. .............................. 548/136; 252/299.01; 252/299.61
[58] Field of Search ............ 252/299.61, 299.01, 252/299.5; 350/350 R, 350 S; 548/136, 142

[56] References Cited

FOREIGN PATENT DOCUMENTS

| | | |
|---|---|---|
| 3515373 | 11/1986 | Fed. Rep. of Germany ........................ 252/299.61 |
| 117014 | 12/1975 | German Democratic Rep. ................. 252/299.61 |
| 240385 | 10/1986 | German Democratic Rep. ................. 252/295.61 |
| 240386 | 10/1986 | German Democratic Rep. ................. 252/299.61 |
| 247221 | 7/1987 | German Democratic Rep. ................. 252/299.61 |
| 247694 | 7/1987 | German Democratic Rep. ................. 252/299.61 |
| 88/08019 | 10/1988 | World Int. Prop. O. ...... 252/299.61 |

OTHER PUBLICATIONS

Demus, D., et al., Flussige Kristalle in Tabellen II, VEB Deutscher Verlag für Grundstoffindustrie, Leipzig, pp. 359–361 (1984).
Dimitrowa, K., et al., J. Prakt, Chemie, vol. 322, No. 6, pp. 933–944 (1980).
Gray, G. W., et al., Liquia Crystals & Plastic Crystals, vol. 1, John Wiley & Sons, Inc., N.Y., pp. 142–143 (1974).

*Primary Examiner*—John S. Maples
*Assistant Examiner*—Richard Treanor
*Attorney, Agent, or Firm*—Jordan and Hamburg

[57] ABSTRACT

2,5-substituted 1,3,4-thiadiazoles of the general formula

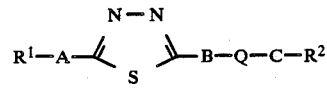

The aforementioned compounds are used in amounts of 0.1 to 80 mole percent in mixtures for electrooptical arrangements for the modulation of transmitted and reflected light, as well as for the colored or black-and-white display of numerals, symbols and moving or still pictures. The compounds endow the liquid-crystalline mixtures with an extended phase field of the smectic C phase, negative dielectric anisotropy and the property of forming optically active C phases upon admixture with optically active compounds.

12 Claims, No Drawings

LIQUID-CRYSTALLINE, 2,5-DISUBSTITUTED, 1,3,4-THIADIAZOLES WITH EXTENDED SMECTIC C PHASES

BACKGROUND OF THE INVENTION

The invention relates to chiral or achiral liquid crystals, preferably with extended smectic C phases for liquid-crystalline mixtures for electrooptical arrangements for the modulation of the transmitted or reflected light, as well as for the colored or black-and-white display of numerals, symbols and moving or still pictures.

It is well known that liquid-crystalline substances can be used for the modulation of light as well for the display of measured values or for the reproduction of information. This is based on the fact that the preferred orientation of thin layers of the crystalline-liquid substances can be changed by the application of an electrical field. This change in the preferred orientation of crystalline-liquid substances is associated with a change in the optical behavior (birefringence, rotation capability, light absorption). Depending on the initial orientation, the dielectric and optical anisotropy, the conductivity, the spontaneous polarization and the dichroism, which are achieved by the special pretreatment of the electrodes or the addition of suitable substances, as well as on the strength, direction and frequency of the applied electrical field, different types of electrooptic effects are observed and used technically (M. Tobias: International Handbook of Liquid Crystal Displays 1975-76, London; Ovum Ltd., London; G. Meier, E., Sackmann, J. G. Grabmeyer: Applications of Liquid Crystals, Springer-Verlag Berlin-Heidelberg-New York 1975; N. A. Clark, S. T. Lagerwall: Appl. Phys. Lett. 36, 899 (1980)).

For example, a known method is based on the fact that, by the application of an electric field to a substance with an optically active smectic C phase, the average direction of the longitudinal axes of the molecules and twice the tilt angle, can be changed. The rapid switching over, which occurs at the same time, can be observed, for example, for incident light, with the help of polarization as a strong intensity change.

For the technical application of ferroelectric smectic C phases, the substances used must fulfill certain conditions, such as extended, optically active smectic C phases
chemical stability and
a negative dielectric anisotropy.

Since mixtures are used almost exclusively for the technique, it is necessary to find mixture components which, on the one hand, have high transition temperatures of the C phase into other phases and, on the other, at lower temperatures, including the supercooled regions, have no additional liquid crystalline phases. In this connection, it is not absolutely essential that these components be optically active themselves. It is only necessary that, in mixtures with optically active $S_C$ phases or other optically active substances, they form optically active mixtures.

SUMMARY OF THE INVENTION

It is an objective of the invention to provide new crystalline-liquid substances for mixtures of liquid-crystalline substances for electrooptical applications with an extended range.

It is a further object of the invention to provide suitable mixing components with an extended phase field of the smectic C phase, negative dielectric anisotropy and the property of forming optically active phases in mixtures. Pursuant to the invention, chiral or achiral crystalline-liquid 2,5-disubstituted 1,3,4-thiadiazoles, which preferably form smectic C phases and have the general formula I

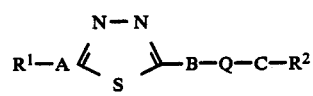

wherein

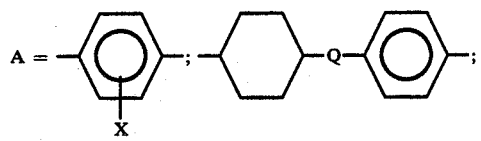

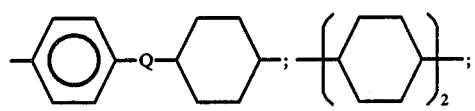

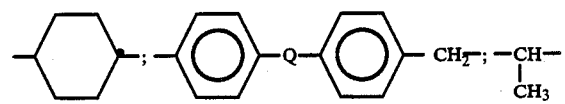

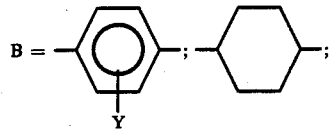

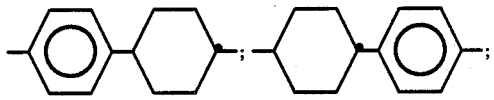

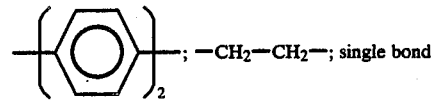

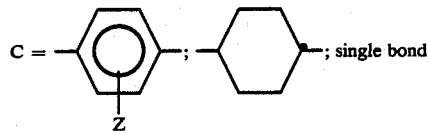

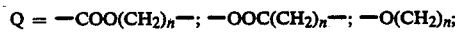

with n = 0 ... 4

X, Y, Z = independently of one another —H, —CN, —Cl, Br, F, —OCH$_3$, —OC$_2$H$_5$, —CH$_3$, —C$_2$H$_5$ or —Q—C— also represents

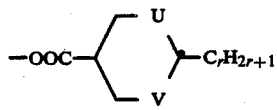

with U, V=O,O; O,S; or S,S and r=1 ... 12
or —Q—C— represents a single bond, R²=—OOCR³ or —COOR³ and R¹, R², and R³ in each case represent linear or branched alkyl chains with 2 to 20 carbon atoms, in which one CH₂ group, which is not adjacent to a hetero atom, may be replaced by O, S, —OOC—, —COO—, —OOCO— or —CH=CH—

R² may also represent

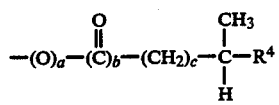

with
R⁴=—$C_mH_{2m+1}$, —$OC_{m-1}H_{2m-1}$
and m=1 to 16
a,b=0 or 1
c=0 to 6.

In mixtures with one another as well as with other crystalline-liquid or noncrystalline-liquid substances, preferably in which compounds of the invention constitute 0.1 to 80 mole percent of the mixture, they are suitable for use in rapidly switching optoelectronic components with memory properties.

The 2,5-disubstituted 1,3,4-thiadiazoles of the invention have broad, chiral S₀ regions of existence with low melting temperatures and, in particular, high clarifying temperatures.

The new substances are stable to heat, irradiation with visible and ultraviolet light and direct and alternating electrical fields. In contrast to the previously known derivatives of 2,5-disubstituted thiadiazoles (D. Demus, H. Zaschke; Liquid Crystals in Tables II, pages 359-361; published by VEB Deutsches Verlag feur Grundstoffindustrie, Leipzig, 1984), they have broad, smectic C phase ranges.

The substances can be used particularly advantageously in mixtures with one another as well as with other ferroelectric crystalline-liquid substances, for inducing ferroelectric properties in achiral compounds with smectic mesophases as well as for inducing smectic C phases.

A further advantage of the substances of the invention lies therein that in many of them no additional smectic phases occur below the smectic C phase even with supercooling.

The substances may be obtained by known methods by the reaction of carboxylic hydrazides with acid chlorides, especially chiral 4-alkyloxybenzoyl chlorides or achiral 4-acyloxy-benzoyl chlorides, and subsequent sulfurization with P₄S₁₀ in organic solvents, especially in pyridine, or in the absence of these:

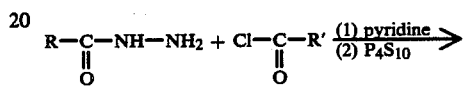

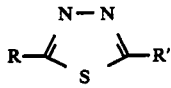

The reaction of achiral 4-acyloxy-benzoyl chlorides with carboxylic hydrazides leads to achiral 4-(4-acyloxyphenyl)-thiadiazoles, which are substituted in the 2 position and are at first saponified according to the following reaction outline to the corresponding phenols and subsequently esterified once again directly with chiral carboxylic acids or by means of their acid chloride.

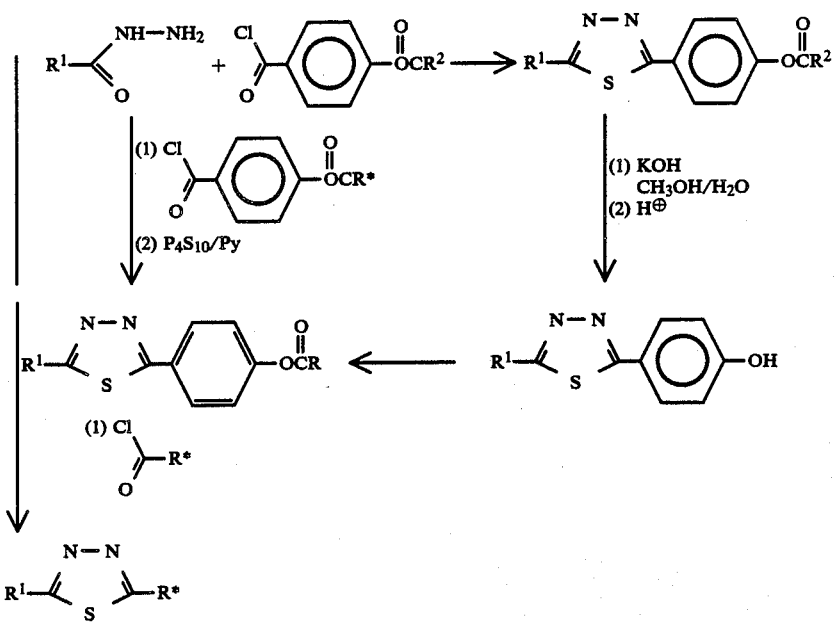

The chiral carboxylic acids are synthesized, for example, by oxidation of chiral alcohols (such as (S)-isoamyl alcohol)

by asymmetric synthesis, for example, by means of chiral oxazolones or chiral imides by etherification of 4-hydroxybenzoic acid with chiral alkyl halides or tosylates by esterification of 4-hydroxybenzaldehyde with chiral carboxylic acids and subsequent oxidation or by direct esterification of 4-hydroxybenzoic acid by alkylation of chiral α-hydroxycarboxylic acids (such as lactic acid) and their derivatives.

DETAILED DESCRIPTION OF PREFERRED EMBODIMENTS OF THE INVENTION

EXAMPLE 1

(S)-2-(4-n-Octyloxyphenyl)-5-[4-(2-methylbutanoyloxy)-phenyl]-thiadiazole

A solution of 2.64 g (0.01 moles) of 4-n-octylbenzoic acid hydrazide in 30 mL absolute pyridine was treated dropwise at 0°-5° C. with stirring with 2.4 g (0.01 moles) (S)-4-(2-methylbutanoyloxy)-benzoyl chloride. The reaction mixture is stirred subsequently for 45 minutes at 0° C., 45 minutes at 20° C. and 3 hours at 80° C.

After cooling to room temperature, 3 g of $P_4S_{10}$ are added and, after the exothermic reaction has subsided, stirring was continued for 1 hour at 80° C. C and 12 hours at 100° C. C.

After cooling to room temperature, 10 mL of ethanol were added and the reaction mixture poured into 200 mL of ice water.

The solution was neutralized with aqueous NaOH and the reaction product filtered off with suction, washed with water and recrystallized from ethanol.

Yield: 2.8 g=60% of the theoretical.

Further compounds were synthesized according to this procedure (see Tables 1 and 3).

EXAMPLE 2

(S)-2-(2-Methylpropyl)-5-(4-n-octyloxyphenyl)-thiadiazole (Compound ½)

Following the procedure of Example 1, 2.64 g (0.01 moles) of 4-n-octyloxybenzoic acid hydrazide were reacted with 1.20 g (0.01 moles) of (S)-2-methylbutyryl chloride.

Yield: 2.7 g=74% of the theoretical=0.0074 moles

EXAMPLE 3

2-(4-n-pentyloxyphenyl)-5-(4-hydroxyphenyl)-thiadiazole 2-(4-n-pentyloxyphenyl)-5-(4-acetyloxyphenyl)-thiadiazole 4.0 g (0.01 moles) was suspended in 40 mL methanol and mixed with a solution of 2.0 g KOH in 90 mL methanol. The mixture was heated for 2 hours under reflux. The solvent was subsequently distilled off in a rotary evaporator and the residue dissolved in 50 mL water. The solution was acidified with 5% HCl, and the precipitate formed was filtered off with suction and recrystallized from ethanol.

Yield: 3.2 g=94% of the theoretical.

The following compounds were synthesized by this procedure:

| | Melting Point in °C. |
|---|---|
| $C_5H_{11}O$—⟨phenyl⟩—thiadiazole—⟨phenyl⟩—OH | 194 |
| $C_8H_{17}O$—⟨phenyl⟩—thiadiazole—⟨phenyl⟩—OH | |
| $C_9H_{19}O$—⟨phenyl⟩—thiadiazole—⟨phenyl⟩—OH | 193 |
| $C_7H_{15}$—thiadiazole—⟨phenyl⟩—OH | 100–101 |
| $C_{10}H_{21}$—⟨phenyl⟩—thiadiazole—⟨phenyl⟩—OH | 152–153 |

EXAMPLE 4

(S)-2-[4-(2-Hexyloxypropanoyloxy)-phenyl]-5-(4-n-pentyloxyphenyl)-thiadiazole 2-(4-n-Pentyloxyphenyl)-5-(4-hydroxyphenyl)-thiadiazole 0.36 g (1 mmole), 2.6 g (1.5 mmole) (S)-hexyloxypropanoic acid, 0.4 g (1.3 mmoles) EDC methiodide and 10 g DMAP were suspended in 5 mL of $CH_2Cl_2$ and stirred for 20 hours at room temperature.

The resulting solution is diluted with 100 mL $CH_2Cl_2$ and washed twice with 100 mL water and once with 100 mL of a 5% sodium bicarbonate solution. The solvent is distilled off in a rotary evaporator and the residue recrystallized from ethanol.

Yield: 0.35 g of 70% of the theoretical.

Further compounds were synthesized according to this procedure (see Tables 1, 2, 3)

TABLE 1

$R^1$—⟨phenyl⟩—thiadiazole—$R^2$

| Nr. | $R^1$ | $R^2$ | K | $S_A$ is |
|---|---|---|---|---|
| 1/1 | $C_6H_{13}O$—*C(CH_3)—COO— | —$C_9H_{19}$ | | |
| 1/2 | $C_8H_{17}O$— | —*CH(CH_3)—$C_2H_5$ | . 52 | (. 19) . |

TABLE 1-continued

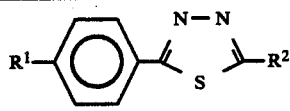

| Nr. | R¹ | R² | K | S_A | is |
|---|---|---|---|---|---|
| 1/3 | C₂H₅—*CH(CH₃)—COO— | —C₇H₁₅ | . 53.5 | — — | . |
| 1/4 | CH₃O—*CH(CH₃)—COO— | —C₇H₁₅ | . 55 | — — | . |
| 1/5 | C₆H₁₃O—*CH(CH₃)—COO— | —⟨H⟩—C₂H₅ | . 75 | (.01) | . |

K = crystalline, solid
S_A, S_C = smectic A-, C-phase
CH = cholesterinic phase
is = isotropic-liquid

TABLE 2

| Nr. | n | K | S_C | S_A | CH | is |
|---|---|---|---|---|---|---|
| 2/1 | 7 | . 103 | . 115 | — — | . 166 | . |
| 2/2 | 9 | | | | | |

TABLE 3

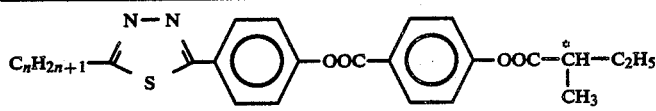

| Nr. | R¹ | R² | K | S_C* | CH | is |
|---|---|---|---|---|---|---|
| 3/1 | C₁₀H₂₁— | —C₂H₅ | . 126 | . 140 | — — | . |
| 3/2 | C₁₀H₂₁— | —OCH₃ | . 108 | . 139 | . 139.5 | . |
| 3/3 | C₁₀H₂₁— | —OC₆H₁₃ | . 110 | . 121 | — — | . |
| 3/4 | C₅H₁₁O— | —C₂H₅ | . 155 | . 161 | . 163 | . |
| 3/5 | C₅H₁₁O— | —OCH₃ | . 96 | . 155 | . 165 | . |
| 3/6 | C₅H₁₁O— | —OC₆H₁₃ | . 93 | . 138 | — — | . |
| 3/7 | C₅H₁₁O— | —OC₁₀H₂₁ | . 92 | . 133 | — — | . |
| 3/8 | C₈H₁₇O— | —C₂H₅ | . 89 | . 163 | — — | . |
| 3/9 | C₈H₁₇O— | —OC₆H₁₃ | . 85 | . 143.5 | — — | . |
| 3/10 | C₈H₁₇O— | —OC₁₀H₂₁ | . 80 | . 134.5 | — — | . |
| 3/11 | C₉H₁₉O— | —OCH₃ | . 101 | . 163 | . 166 | . |
| 3/12 | C₉H₁₉O— | —OC₆H₁₃ | . 78 | . 144.5 | — — | . |

EXAMPLE 5

Synthesis of 2-(4-n-octyloxyphenyl)-5-(4-[trans-4-n-propylcyclohexylpropionyloxy]phenyl)-1,3,4-thiadiazole 2-(4-n-Octyloxyphenyl)-5-(4-hydroxyphenyl)-1,3,4-thiadiazole (0.1 mole, 3.82 g) is suspended in 50 mL of absolute toluene and, after addition of 10 mL triethylamine and 100 mg 4-dimethylaminopyridine, treated with stirring with 0.011 moles (2.38 g) 3-(trans-4-n-propylcyclohexyl)-propionyl chloride. The mixture is stirred for 12 hours at room temperature and for 2 hours at 80° C. After being allowed to cool to room temperature, the reaction solution is diluted with 100 mL ether and washed once with 100 mL water, once with 100 mL 5% sodium bicarbonate solution and once again with 100 mL water. After drying over Na₂SO₄, the solvent is distilled off in a rotary evaporator. The residue is recrystallized from ethanol and methanol until the transition temperature is constant.

Yield: 4.2 g (0.0075 moles)=75% of the theoretical.

Synthesis of 2-(4-n-octyloxyphenyl)-5-(4-acetoxyphenyl)-1,3,4-thiadizaole 4-n-Octyloxybenzoic acid hydrazide (0.1 moles, 26.4 g) is dissolved in 300 mL absolute pyridine and treated dropwise at 0° to 5° C. with stirring with 0.1 moles (19.8 g) 4-acetoxybenzoyl chloride.

The reaction mixture is allowed to warm up slowly to room temperature and then stirred first for 2 hours at 20° C. and subsequently for 2 hours at 70° C.

After it has cooled to room temperature, the reaction mixture is poured into 1 L of ice water. The precipitate is washed with water and recrystallized once from ethanol.

Yield: 38 g (0.09 moles)=90% of the theoretical.

The N-(4-n-Octyloxybenzoyl)-N'-(4-acetoxybenzoyl)-hydrazine (0.05 moles, 21,3 g), so obtained, is dissolved in 150 mL of pyridine and treated with stirring with 15 g of P₄S₁₀.

After the exothermic reaction has subsided, the temperature is raised for 2 hours to 80° C. and stirring is continued for a further 12 hours at 100° C. After cooling to room temperature, 50 mL of ethanol are added and the reaction mixture is poured into 1 L of ice water. The solution obtained is neutralized with 10% sodium hydroxide solution and the reaction product is filtered off with suction. The reaction product is washed thoroughly with water and recrystallized from ethanol or methanol.

Yield: 18.1 g (0.0426 moles) = 85% of the theoretical.

The substances named in the following were obtained in a similar manner.

I

| Nr. | $R^1$ | $R^2$ | K | S | $S_C$ | $S_A$ | N | is |
|---|---|---|---|---|---|---|---|---|
| I 1 | $C_{10}H_{21}$ | $CH_3$ | .117 | — — | .134 | — — | .183 | . |
| I 2 | $C_{10}H_{21}$ | $OC_7H_{15}$ | .80 | — — | .153 | — — | .157 | . |
| I 3 | $C_{10}H_{21}$ | $OC_4H_9$ | .64 | — — | .146 | .147 | .166 | . |
| I 4 | $OC_5H_{11}$ | $C_2H_5$ | .118 | — — | .161 | .162 | .225 | . |
| I 5 | $OC_5H_{11}$ | $OC_4H_9$ | .95 | — — | .141 | — — | .196 | . |
| I 6 | $OC_8H_{17}$ | $CH_3$ | .116 | — — | .170 | — — | .213 | . |
| I 7 | $OC_8H_{17}$ | $C_2H_5$ | .113 | — — | .169 | — — | .209 | . |
| I 8 | $OC_8H_{17}$ | $C_9H_{19}$ | .90 | — — | .194 | — — | — — | . |
| I 9 | $OC_8H_{17}$ | $CH_2OC_7H_{15}$ | .87 | — — | .197 | — — | — — | . |
| I 10 | $OC_8H_{17}$ |  $CH_2CH_2$—⟨ ⟩—$C_3H_7$ | .90 | (.75) | .216 | — — | .249 | . |
| I 11 | $OC_8H_{17}$ |  $CH_2$—⟨ ⟩—$C_3H_7$ | .130 | — — | .202 | — — | .204 | . |
| I 12 | $OC_8H_{17}$ | $CH(CH_3)C_8H_{17}$ | .65 | (.64) | .135 | — — | — — | . |
| I 13 | $OC_9H_{19}$ | $OC_7H_{15}$ | .83 | — — | .174 | — — | .183 | . |
| I 14 | $OC_9H_{19}$ | $OC_9H_{19}$ | .94 | — — | .198 | — — | — — | . |
| I 15 | $OC_9H_{19}$ | $OC_4H_9$ | .87 | — — | .168 | — — | .186 | . |

S - smectic phase, not characterized further (e.g. in the case I 10 $S_G$).
N - nematic

II

| Nr. | n | R | K | S | $S_C$ | $S_A$ | N | is |
|---|---|---|---|---|---|---|---|---|
| II 1 | 5 | —⟨ ⟩—$C_{10}H_{21}$ | .104 | — — | .121 | .135 | .146 | . |
| II 2 | 7 | —⟨ ⟩—$C_{10}H_{21}$ | .105 | — — | .140 | .141 | .143 | . |
| II 3 | 7 | —⟨ ⟩—$OC_8H_{17}$ | .100 | — — | .159 | — — | .171 | . |
| II 4 | 9 | —⟨ ⟩—$C_{10}H_{21}$ | .103 | — — | .143 | — — | — — | . |
| II 5 | 9 | —⟨ ⟩—$OC_8H_{17}$ | .98 | — — | .166 | — — | .170 | . |

-continued

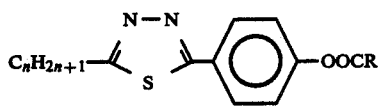

| Nr. | n | R | K | S | $S_C$ | $S_A$ | N | is |
|---|---|---|---|---|---|---|---|---|
| II 6 | 9 | –⟨phenyl⟩–OC$_4$H$_9$ | .105 | — | — | .133 | — — | .173 . |
| II 7 | 9 | –⟨phenyl, C$_2$H$_5$⟩–OC$_5$H$_{11}$ | .81 | — | — | .85 | — — | .99 . |
| II 8 | 9 | –CH$_2$–⟨cyclohexyl⟩–C$_3$H$_7$ | .77 | — | — | .81 | .89 | — — . |
| II 9 | 9 | –CH$_2$–CH$_2$–⟨cyclohexyl⟩–C$_4$H$_9$ | .72 | — | — | .119 | .142 | — — . |
| II 10 | 9 | –CH$_2$–CH$_2$–⟨cyclohexyl⟩–C$_3$H$_7$ | .83 | .105 | .112 | .130 | — — | . |

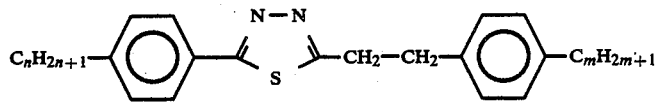

| Nr. | n | m | K | $S_C$ | $S_A$ | N | is |
|---|---|---|---|---|---|---|---|
| II 1 | 6 | 4 | .56 | .89 | .123 | — — | . |

EXAMPLE 6

Synthesis of 2-n-nonyl-5-(4-methoxycarbonylphenyl)-1,3,4-thiadiazole

Decanoic acid hydrazide (0.1 mole, 18.6 g) is reacted as described in Example 5 with 0.1 moles (18.9 g) methoxycarbonylbenzoyl chloride to form N-decanoyl-N'-(4-methoxycarbonylbenzoyl)-hydrazine.

The diacylhydrazine so obtained (0.05 moles, 18.6 g) is reacted as described in Example 5 with 15 g of $P_4S_{10}$.

Yield: 15.0 g (0.041 moles)=82% of the theoretical. Melting point: 114° C.

Synthesis of 4-(2-n-nonyl-1,3,4-thiadiazole-5-yl)-benzoic acid

2-Nonyl-5-(4-methoxycarbonylphenyl)-1,3,4-thiadiazole (0.02 moles, 7.4 g) is added to a solution of 0.2 moles (11.2 g) KOH in 400 mL methanol and heated for 2 hours at the boiling point. The solvent is distilled of in a rotary evaporator and the residue is dissolved in 200 mL of water and acidified with concentrated hydrochloric acid.

The precipitate formed is filtered off with suction and recrystallized from ethanol.

Yield: 5.8 g (0.017 moles)=87% of the theoretical. Melting point: 255° C. (decomp.)

Synthesis of 4-n-octyloxyphenyl 4-(2-n-nonyl-1,3,4-thiadiazole-5-yl)benzoate 4-(2-n-Nonyl-1,3,4-thiadiazole-5-yl)-benzoic acid (0.005 moles, 1.66 g) is reacted with 5 mL of thionyl chloride and heated 2 hours at the boiling point. After that, the excess thionyl chloride is distilled off in the rotary evaporator and the residue is treated with 0.006 moles (1.33 g) octyloxyphenol, dissolved in 20 mL toluene, 5 mL triethylamine and 100 mg 4-dimethylaminopyridine.

The reaction mixture is stirred for 12 hours at room temperature and for 2 hours at 80° C. After cooling to room temperature, it is diluted with 100 mL ether and washed once with 100 mL water, once with 100 mL 5% sodium bicarbonate solution and once with 100 mL water. After drying with Na$_2$SO$_4$, the solvent is distilled off in the rotary evaporator and the residue is recrystallized from methanol until the transition temperature is constant.

Yield: 2.2 g (4×10⁻³ moles).

recrystallized from acetone until the transition temperatures are constant.

Yield: 3.9 g (0.013 moles)=84% of the theoretical.
The following Table gives examples.

$$R^1 \underset{S}{\overset{N-N}{\diagup\!\!\!\diagdown}} \text{—}\bigcirc\text{—}OR^2 \qquad V$$

| Nr. | R¹ | R² | K | S | S_C | S_A | N | is |
|---|---|---|---|---|---|---|---|---|
| V 1 | C₇H₁₅ | CH₂—⬡—C₃H₇ | .109 | — | — | — | .165 | — |
| V 2 | C₇H₁₅ | CH₂—◯—OC₆H₁₃ | .108 | .117 | .156 | — | — | — |
| V 3 | C₇H₁₅ | CH₂—⬡—C₇H₁₅ | .84 | .142 | — | — | .160 | — |
| V 4 | C₇H₁₅ | CH₂—◯—C₇H₁₅ | .95 | — | — | .124 | .140 | — |

The transition temperatures of two compounds are given as example:

$$R^1 \underset{S}{\overset{N-N}{\diagup\!\!\!\diagdown}} \text{—}\bigcirc\text{—}COOR^2 \qquad IV$$

| Nr. | R¹ | R² | K | S_C | S_A | N | I |
|---|---|---|---|---|---|---|---|
| IV 1 | C₁₀H₂₁—◯— | —CH₃ | .140 | — | — | .224 | — |
| IV 2 | C₉H₁₉— | —◯—OC₈H₁₇ | .97 | .131 | .136 | — | — |

EXAMPLE 7

Synthesis of 2-n-heptyl-5-[4-(4-n-heptylphenylmethyleneoxy)-phenyl]-1,3,4-thiadiazole A mixture of 0.01 moles (2.76 g) 2-n-heptyl-5-(4-hydroxyphenyl)-1,3,4-thiadiazole (0.01 moles, 2.76 g), 0.015 moles (4.03 g) 4-n-heptylbenzyl bromide, 50 mL acetone and 15 g potassium carbonate is heated to reflux for 6 hours with stirring.

After the reaction mixture has cooled down, the solid precipitate is filtered off and washed carefully with 100 mL of chloroform. The solution obtained is evaporated to dryness in a rotary evaporator and the residue is

EXAMPLE 8

Synthesis of 2-(trans-4-n-hexylcyclohexyl)-5-[4-(trans-4-n-hexylcyclohexylcarbonyloxy)-phenyl]-1,3,4-thiadiazole 4-Hydroxybenzoic acid hydrazide (0.01 moles, 1.52 g) are reacted as in Example 5 with 0.025 moles (5.75 g) of trans-4-n-hexylcyclohexanecarboxylic acid chloride to form N-(trans-4-n-hexylcyclohexylcarbonyl)-N'-4-(trans-4-n-hexylcyclohexylcarbonyloxy)-benzoylhydrazine.

The diacyl hydrazine so obtained (0.005 moles, 2.7 g) is reacted with 1.5 g of P₄S₁₀ as in Example 5.

Yield: 2.1 g=78% of the theoretical.
Examples are given in the following Table.

VI $C_nH_{2n+1}$—⌬—C(=N—N=)—S—⌬—⌬—OOC—⌬—$C_mH_{2m+1}$

| Nr. | n | m | K | $S_A$ | N | is |
|---|---|---|---|---|---|---|
| VI 1 | 6 | 6 | . 112 | . 159 | . 166 | . |
| VI 2 | 8 | 8 | . 105 | . 161 | — — | . |

EXAMPLE 9

A mixture of

| Component | I 8 | I 2 | II 2 | I 5 | II 3 | II 5 |
|---|---|---|---|---|---|---|
| % by weight | 16.5 | 16.6 | 12.0 | 14.8 | 20.4 | 19.7 | shows the transition schedule
Kr 42 $S_c$ 158 N 172 is

It was established by calorimetric and microscopic investigations that there is no additional phase transition between 158° C. and 30° C.

EXAMPLE 10

The expansion of the $S_C$ phase domain of 4'-n-pentyloxyphenyl 4-n-octyloxybenzoate (K 58 $S_C$ 63 $S_A$ 65 N 85 is) is clearly illustrated by the following example. To 41.9% by weight of the components named, 12.4% component I 7, 23.3% of component II 3 and 22.4% of component II 5 were added. The resulting mixture melts at 40°–45° C. The $S_C$ phase now is stable up to 100° C. The subsequent nematic phase clarifies at 132° C. No further phase transition could be observed below 100° C. on cooling to the crystallization at 32° C.

EXAMPLE 11

To the mixture of Example 10, 7.0% by weight Tigogenin were added. The optically active C phase transforms at 105° C. into the cholesterinic phase.

The optically active smectic C phase could be identified very well by the fan texture, which was interrupted by equidistant lines.

EXAMPLE 12

In a nematic basic mixture ($\Delta\epsilon_{GM}$ 0.314, $T-T_{N/is}=-20K$) 5 mole percent of substance No. I 5 were dissolved. In so doing, the dielectric anisotropy fell by $T-T_{N/is}=-20K$ to $\Delta\epsilon=-0.477$.

Assuming the primitive mixing rule applies, the dielectric anisotropy of the dissolved substance at $T-T_{N/is}$ is calculated to be $\Delta\epsilon(I\ 5)=-3.3$.

EXAMPLE 13

By mixing several inventive substances, the melting points of the ferroelectric crystalline-liquid material are lowered and the existence region expanded appreciably.

This is shown by the following two mixtures:

Mixture 1

Nr. 3/9   $C_8H_{17}O$—⌬—C(=N—N=)—S—⌬—OOC—*CH(—$OC_6H_{13}$)—$CH_3$   50 Mol-%

Nr. 3/10  $C_8H_{17}O$—⌬—C(=N—N=)—S—⌬—OOC—*CH(—$OC_{10}H_{21}$)—$CH_3$   50 Mol-%

K 60–65 $S_C^*$ 133–134 Is

Mixture 2

Nr. 3/9   $C_8H_{17}O$—⌬—C(=N—N=)—S—⌬—OOC—*CH(—$OC_6H_{13}$)—$CH_3$   50 Mol-%

Nr. 3/5   $C_5H_{11}O$—⌬—C(=N—N=)—S—⌬—OOC—*CH(—$OCH_3$)—$CH_3$   50 Mol-%

K 70 $S_C^*$ 146–47 N* 156–57 Is

These two mixtures can be used in optoelectronic displays.

EXAMPLE 14

The following three mixtures are intended to confirm this:

Mixture 3

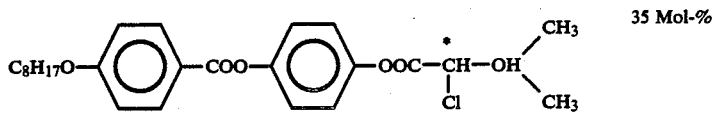 35 Mol-%

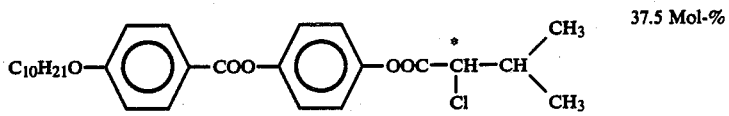 37.5 Mol-%

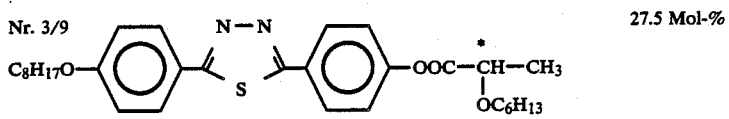 27.5 Mol-%

K 37 $S_C^*$ 60 $S_A$ 84 N* 90 Is

Mixture 4

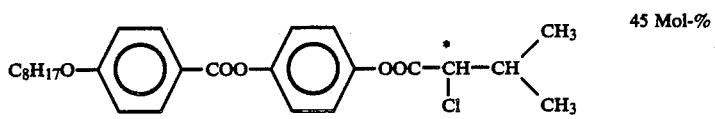 45 Mol-%

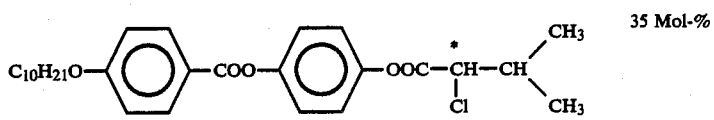 35 Mol-%

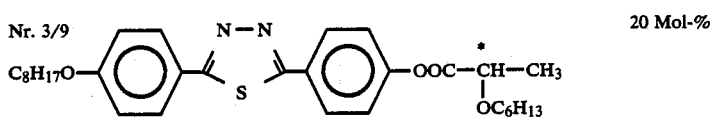 20 Mol-%

K 33 $S_C^*$ 46 $S_A$ 78 N* 81,5 Is

Mixture 5

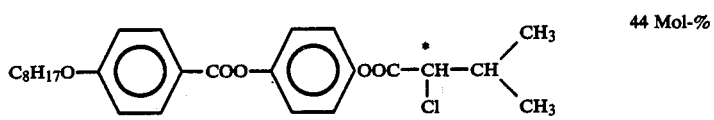 44 Mol-%

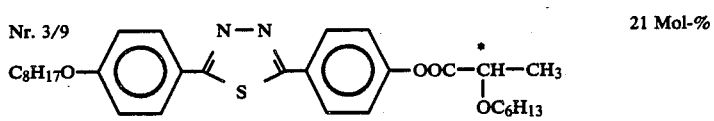 21 Mol-%

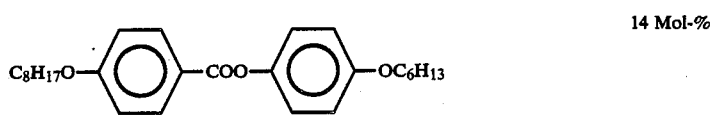 14 Mol-%

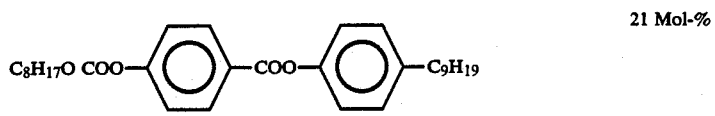 21 Mol-%

K 25 $S_C^*$ 47 $S_A$ 70 N* 79 Is

The properties of the inventive substances are modified substantially by mixing with additional substances, preferably those, which themselves have ferroelectric smectic C* phases or nonchiral C phases.

These mixtures are also well suited for use in displays

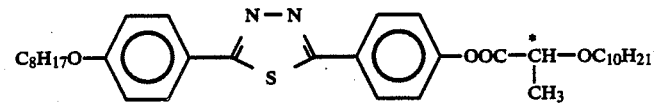

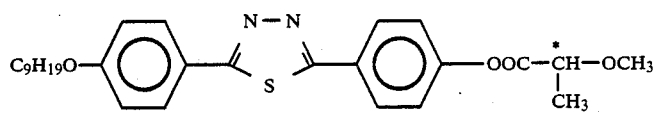
12. A liquid crystalline compound of formula
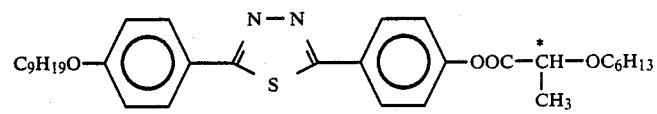

We claim:

1. A liquid crystalline compound of the formula

2. A liquid crystalline compound of the formula

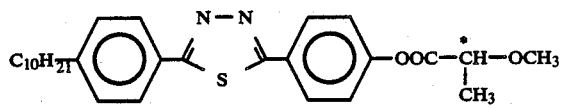

3. A liquid crystalline compound of formula

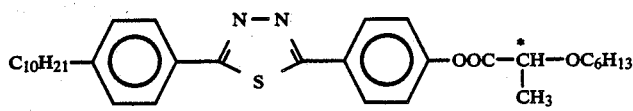

4. A liquid crystalline compound of formula

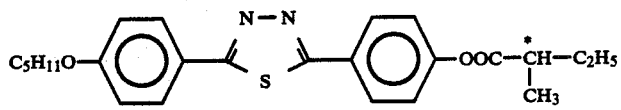

5. A liquid crystalline compound of formula

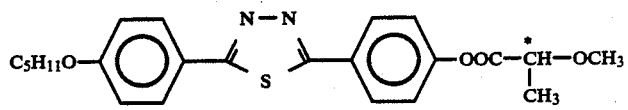

6. A liquid crystalline compound of formula

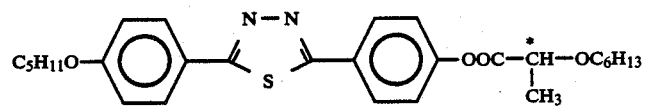

7. A liquid crystalline compound of formula

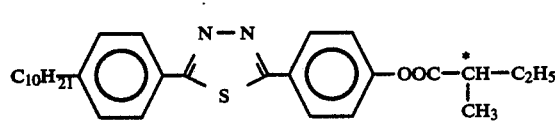

8. A liquid crystalline compound of formula

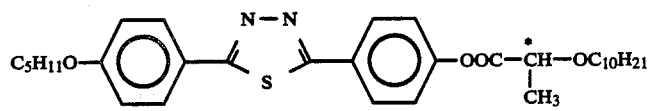

9. A liquid crystalline compound of formula

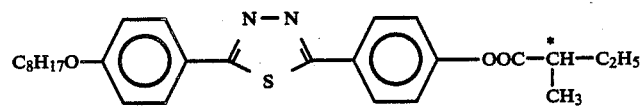

10. A liquid crystalline compound of formula

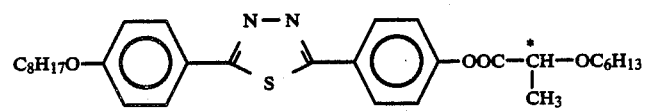

11. A liquid crystalline compound of formula